(12) United States Patent
Simchony et al.

(10) Patent No.: US 9,820,634 B2
(45) Date of Patent: Nov. 21, 2017

(54) INTEGRATED STEERING DEVICE

(71) Applicant: G.I. VIEW LTD., Ramat Gan (IL)

(72) Inventors: Tal Simchony, Hod Ha Sharon (IL); Avraham Sinay, Petach-Tikva (IL); Ilia Krivoruk, Haifa (IL)

(73) Assignee: G.I. VIEW LTD., Ramat Gan (IL)

( * ) Notice: Subject to any disclaimer, the term of this patent is extended or adjusted under 35 U.S.C. 154(b) by 0 days.

(21) Appl. No.: 14/761,915

(22) PCT Filed: Jan. 21, 2014

(86) PCT No.: PCT/IL2014/050067
§ 371 (c)(1),
(2) Date: Jul. 17, 2015

(87) PCT Pub. No.: WO2014/111943
PCT Pub. Date: Jul. 24, 2014

(65) Prior Publication Data
US 2015/0359416 A1    Dec. 17, 2015

Related U.S. Application Data

(60) Provisional application No. 61/754,716, filed on Jan. 21, 2013.

(51) Int. Cl.
*A61B 1/00* (2006.01)
*A61B 1/005* (2006.01)
(Continued)

(52) U.S. Cl.
CPC .......... *A61B 1/0055* (2013.01); *A61B 1/0057* (2013.01); *A61B 1/00114* (2013.01);
(Continued)

(58) Field of Classification Search
USPC ................................................ 600/139–146
See application file for complete search history.

(56) References Cited

U.S. PATENT DOCUMENTS 3,998,216 A    12/1976  Hosono
4,432,349 A    2/1984   Oshiro
(Continued)

FOREIGN PATENT DOCUMENTS

CN    102469917    5/2012
CN    102596064    7/2012
(Continued)

OTHER PUBLICATIONS

International Search Report for International Application No. PCT/IL2014/050067 mailed Aug. 5, 2014.

*Primary Examiner* — Matthew J Kasztejna
(74) *Attorney, Agent, or Firm* — Dorsey & Whitney LLP

(57) ABSTRACT

The present invention discloses a steering device for use in a body lumen of a patient. The steering device comprises a flexible tube; a plurality of spaced-apart elements positioned along at least a portion of the tube; wherein the plurality of spaced-apart elements and the tube form a single integrated unit; and at least two steering wires having at least a portion passing through the spaced-apart elements and at least a portion passing within the tube. According to another broad aspect of the present invention, there is provided a steering device for use in a body lumen of a patient, comprising: a flexible tube; at least two steering wires having at least a portion passing within the flexible tube; at least two spring-like sleeves; each spring-like sleeve at least partially enclosing a steering wire respectively; wherein the spring-like sleeve has a variable pitch along its length; such that the flexible tube comprises at least two portions having different bending properties.

21 Claims, 9 Drawing Sheets

(51) Int. Cl.
*A61M 25/01* (2006.01)
*A61B 1/012* (2006.01)
*A61B 1/015* (2006.01)
*A61B 1/018* (2006.01)
*A61B 1/04* (2006.01)
*A61B 1/06* (2006.01)
*A61B 1/31* (2006.01)
*A61B 10/04* (2006.01)
*A61B 17/00* (2006.01)
*A61M 25/00* (2006.01)

(52) U.S. Cl.
CPC .............. *A61B 1/015* (2013.01); *A61B 1/018* (2013.01); *A61B 1/0125* (2013.01); *A61B 1/04* (2013.01); *A61B 1/06* (2013.01); *A61B 1/31* (2013.01); *A61B 10/04* (2013.01); *A61B 17/00234* (2013.01); *A61M 25/0141* (2013.01); *A61M 25/0147* (2013.01); *A61B 2017/0034* (2013.01); *A61B 2017/00314* (2013.01); *A61B 2017/00323* (2013.01); *A61M 25/0032* (2013.01); *A61M 25/0138* (2013.01); *A61M 2025/0036* (2013.01)

(56) References Cited

U.S. PATENT DOCUMENTS

| | | | | |
|---|---|---|---|---|
| 4,686,963 A | * | 8/1987 | Cohen | A61B 1/0055 138/120 |
| 4,700,693 A | | 10/1987 | Lia et al. | |
| 4,770,188 A | * | 9/1988 | Chikama | A61B 1/00154 600/585 |
| 4,826,087 A | * | 5/1989 | Chinery | B05B 13/0431 137/636 |
| 4,911,148 A | * | 3/1990 | Sosnowski | A61B 1/0051 600/136 |
| 5,005,558 A | * | 4/1991 | Aomori | A61B 1/0055 600/141 |
| 5,174,276 A | * | 12/1992 | Crockard | A61B 17/1285 600/104 |
| 5,174,277 A | * | 12/1992 | Matsumaru | A61B 1/0057 600/142 |
| 5,179,935 A | * | 1/1993 | Miyagi | A61B 1/0055 600/108 |
| 5,325,845 A | * | 7/1994 | Adair | A61B 1/0055 600/114 |
| 5,381,782 A | * | 1/1995 | DeLaRama | A61B 1/0056 138/118 |
| 5,520,222 A | * | 5/1996 | Chikama | A61B 1/0055 138/103 |
| 5,679,216 A | | 10/1997 | Takayama et al. | |
| 5,873,817 A | * | 2/1999 | Kokish | A61B 1/0058 600/143 |
| 5,899,914 A | * | 5/1999 | Zirps | A61B 17/1608 606/170 |
| 6,013,024 A | * | 1/2000 | Mitsuda | A61B 1/00039 600/146 |
| 6,270,453 B1 | * | 8/2001 | Sakai | A61B 1/0055 600/141 |
| 6,364,828 B1 | * | 4/2002 | Yeung | A61B 1/0056 174/68.3 |
| 6,875,170 B2 | * | 4/2005 | Francois | A61B 1/0053 600/141 |
| 7,147,650 B2 | * | 12/2006 | Lee | A61B 17/00234 606/1 |
| 7,591,783 B2 | * | 9/2009 | Boulais | A61B 1/00059 600/139 |
| 7,637,905 B2 | | 12/2009 | Saadat et al. | |
| 8,512,228 B2 | * | 8/2013 | Vargas | A61B 1/00154 600/114 |
| 8,550,989 B2 | * | 10/2013 | Dohi | A61B 1/00078 600/114 |
| 9,155,451 B2 | * | 10/2015 | Smith | A61B 1/00078 |
| 2004/0138525 A1 | | 7/2004 | Saadat et al. | |
| 2004/0199052 A1 | | 10/2004 | Banik et al. | |
| 2006/0146127 A1 | * | 7/2006 | Bagley | G02B 23/2492 348/83 |
| 2007/0232858 A1 | | 10/2007 | Macnamara et al. | |
| 2009/0182268 A1 | * | 7/2009 | Thielen | A61M 25/0138 604/95.04 |
| 2009/0234186 A1 | | 9/2009 | Lin et al. | |
| 2010/0324370 A1 | * | 12/2010 | Dohi | A61B 1/00078 600/144 |
| 2012/0053607 A1 | * | 3/2012 | Adams | A61B 17/32056 606/170 |

FOREIGN PATENT DOCUMENTS

CN 102789050 11/2012
EP 2248483 11/2010

* cited by examiner

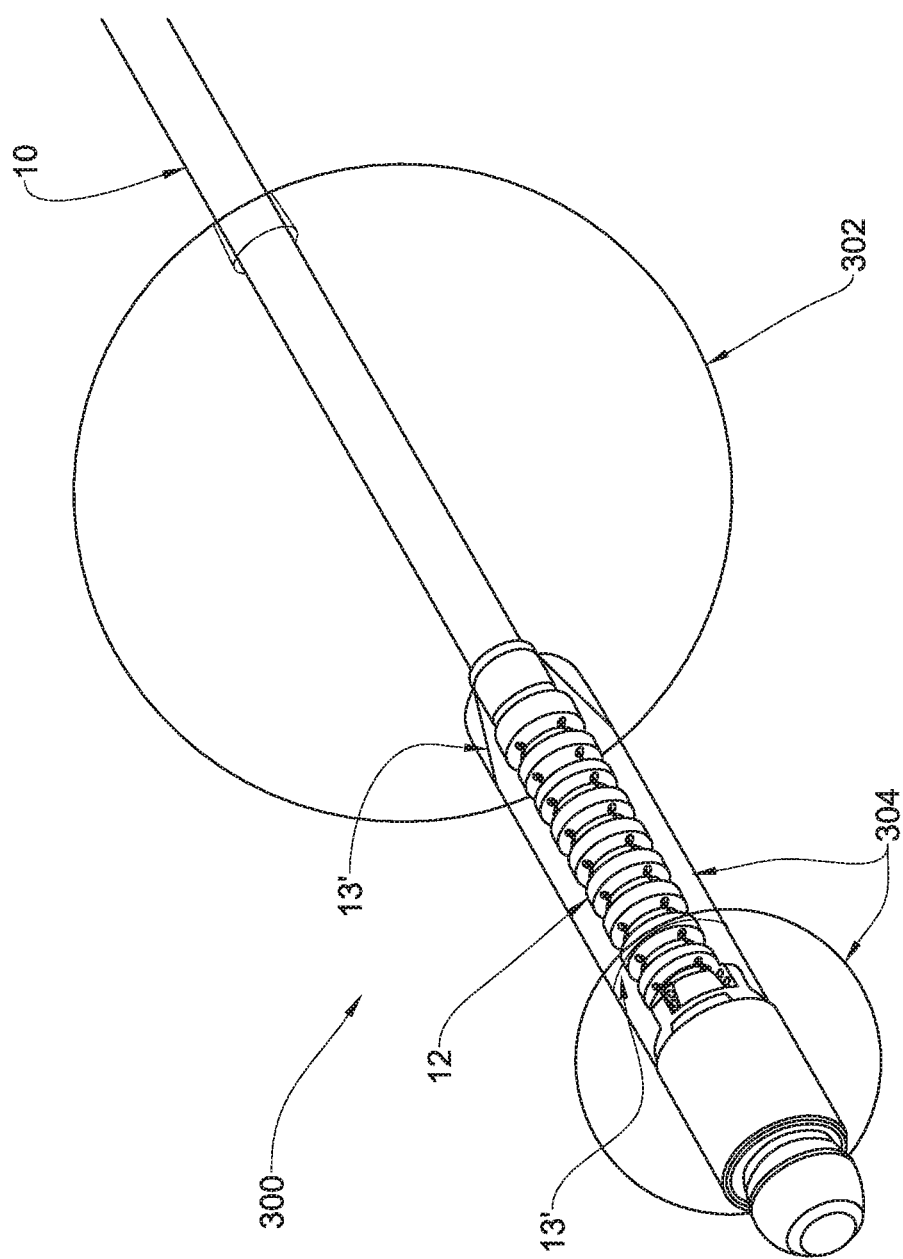

INTEGRATED STEERING DEVICE

FIELD OF THE INVENTION

The present invention relates generally to the field of multidirectional medical instruments, and more specifically, to steerable medical instruments.

BACKGROUND OF THE INVENTION

Endoscopes and imaging catheters are widely used in many medical procedures for viewing areas of bodily organs, cavities, passageways, etc. Generally, such imaging devices include an elongated sheath or similar structure wherein optical fibers are arranged both for transmitting illumination light to the distal end of the sheath to illuminate a viewing field, and for carrying an optical image back to a viewing port or camera. One or more lenses may be positioned on the distal end of the imaging device to focus the optical image received by, or the illumination cast by the instrument.

In many applications, it is desirable that the distal portion of the imaging device be "steerable", bendable or maneuverable from the proximal end of the device to facilitate guidance of the device through tortuous or furcated anatomical passageways. Additionally, the ability to bend the device at or near its distal end may enable the operator to visually scan an expanded viewing area by bending or otherwise manipulating the distal end of the device. The ability to maneuver the tip makes it easier to guide the tip of the device properly through the often highly branched and convoluted passageways near organs.

In order to effect and control the deflection of the distal tip of an imaging device, many designs have been introduced that incorporate either two opposed control wires to control bending in one plane, or four wires evenly spaced to control bending in two perpendicular planes. These control wires run the length of the device and terminate at the distal end of the steerable region or at the distal tip. The proximal end of each control wire is functionally connected to a separate drum or spool rotated manually or by a dedicated electrical or fluid motor for linearly advancing and retracting the control wire in relation to the device. In operation, when one of the control wires is pulled proximally by rotation of the drum or spool, the distal tip of the device bends at the steerable region toward the retracted wire.

As an aid to the early detection of disease, it has become well established that there are major public health benefits from regular endoscopic examinations of internal structures such as alimentary canals and airways, e.g., the esophagus, lungs, colon, uterus, and other organs. A conventional imaging endoscope used for such procedures comprises a flexible tube with a fiber optic light guide that directs illuminating light from an external light source to the distal tip where it exits the endoscope and illuminates the tissue to be examined. Frequently, additional optical components are incorporated to adjust the spread of light exiting the fiber bundle and the distal tip. An objective lens and fiber optic imaging light guide communicating with a camera at the proximal end of the scope, or an imaging camera chip at the distal tip, produce an image that is displayed to the examiner. In addition, most endoscopes include one or more working channels through which medical devices such as biopsy forceps, snares, fulguration probes, and other tools may be passed.

U.S. Pat. No. 5,679,216 describes a multi-degree-of-freedom manipulator including a flexible tube having a plurality of flex portions, a plurality of actuators made of shape memory alloy for flexing the flex portions, two common energy transmission paths for transmitting energy to the actuators, and selective energy supply members for controlling the energy supplied from the common energy transmission path to the actuators, thereby respectively independently driving the actuators to bend the flexible tube.

U.S. Pat. No. 4,432,349 describes an articulated tube structure for use in an endoscope or the like which consists of a number of elementary tubes connected in end-to-end relationship. Between the adjacent elementary tubes are provided springs to urge the articulated tube to bend in one direction. The articulated tube is spring urged in one direction and is manipulated to bend as desired by operation of pull wires extending through the articulated tube and fixed at their end to the head of the endoscope.

Navigating channels in the human body can be very challenging. Some parts of the human anatomy can be difficult to see and are not always oriented in a convenient location relative to the position of the scope or surgical instrument. Occasionally, the anatomy and the degrees of freedom of the instruments can impede or prevent successful navigation. During conventional colonoscopy procedures, a colonoscope is advanced through the tortuous sigmoid colon until the colonoscope reaches the descending colon. The colonoscope is then manipulated to reduce the redundancy in the sigmoid colon. When the sigmoid colon has been straightened, the colonoscope is typically further advanced through the colon. However, this type of procedure is generally difficult to perform, and/or painful for the patient due to stretching of the colon which occurs upon impact between the colonoscope and the wall of the colon as the colonoscope is advanced, especially during advancement of the colonoscope around the bends of the tortuous sigmoid colon. Navigation of the endoscope through complex and tortuous paths is critical to success of the examination with minimum pain, side effects, risk, or sedation to the patient. To this end, modern endoscopes include means for deflecting the distal tip of the scope to follow the pathway of the structure under examination, with minimum deflection or friction force upon the surrounding tissue. Control cables similar to puppet strings are carried within the endoscope body in order to connect a flexible portion of the distal end to a set of control knobs at the proximal endoscope handle. By manipulating the control knobs, the examiner is usually able to steer the endoscope during insertion and direct it to a region of interest, in spite of the limitations of such traditional control systems, which are clumsy, non-intuitive, and friction-limited. Common operator complaints about traditional endoscopes include their limited flexibility, limited column strength, and limited operator control of stiffness along the scope length.

Conventional endoscopes are generally built of sturdy materials, which decrease the flexibility of the scope and thus can decrease patient comfort. Furthermore, conventional endoscopes are complex and fragile instruments that frequently need costly repair as a result of damage during use or during a disinfection procedure. Still, many procedures using steerable instruments remain difficult. A great deal of skill and patience is often required to correctly orient the instrument in a predetermined position.

GENERAL DESCRIPTION

The present invention provides a novel steering device which may be incorporated or coupled to any endoscopic tool, having better navigation and tracking, a superior interface with the operator, improved access by reduced frictional forces upon the lumenal tissue, increased patient comfort, and greater clinical productivity and patient throughput than those that are currently available.

Therefore, according to one broad aspect of the present invention, there is provided a steering device for use in a body lumen of a patient, comprising: a flexible tube; a plurality of spaced-apart elements positioned along at least a portion of the tube; the plurality of spaced-apart elements and the tube forming a single integrated unit; and at least two steering wires having at least a portion passing through the spaced-apart elements and at least a portion passing within the tube. Using the novel configuration of the steering device in which the spaced-apart elements are integrated with a flexible tube and not mounted on another tube enables to provide a steering device with a higher flexibility and in which minimal deflection force has to be applied in order to bend the bending portion of the tube. In addition, this novel invention requires less moving parts, less complicated manufacturing techniques and allows easy and quick installation. It should be understood that conventional steering devices comprise an elongated main body having a scope therethrough.

U.S. Pat. No. 7,637,905 of Saadat describes a steerable tool with at least one steerable tool arm which extends from the distal end of the main body. In this disclosure, the steerable tool arm is a stand-alone unit which can be separated from the main body and is not integrated to the main body. This type of configuration has lower flexibility because the steering device comprises two separate stand-alone elements (e.g. the main body and the steerable arm) made of usually two different materials and constituting two different layers extending along the steering part of the device. Moreover, higher deflection force has to be applied in order to bend the bending portion of the tube, in order to bend the main body as well as the steerable arm creating a higher load. Furthermore, friction forces are created between the main body and the steerable arm layers. To overcome these disadvantages, the novel steering device of the present invention provides a single integrated unit comprising a tube with spaced-apart elements enabling the steering of the device. Moreover, the configuration of the novel steering device of the present invention eliminates stiff mechanical linkages between the adjacent links to ensure bending, and provides a soft tube that can be bent and twisted at any possible direction, thus allowing greater mobility that requires fewer elements.

In some embodiments, the plurality of spaced-apart elements is rigidly fastened along the tube. The fastening of the elements on the tube may be made by any suitable method for example by at least partially coating the element with adhesive material or by ultrasonic welding. Alternatively the elements and the tube may be manufactured to form a single integrated unit. The steering device comprises a plurality of spaced-apart elements threaded via the wires.

It should be understood that the steering device is configured such that, in a straight state, when not bent, the spaced-apart elements do not touch each other. When the tube is in a fully bent state, the spaced-apart elements' edges come into contact.

In some embodiments, the spaced-apart elements are separated by a constant distance between them. In this connection, it should be understood that the distance between the elements determines the properties of the tube, such as its flexibility and bending properties, as well as the shape of the bent tip/distal end of the tube. The distance between the spaced-apart elements is determined according to the specific material of the flexible tube. The distance between the spaced-apart elements is selected in such a way that prevents sharp bends of the tube that may lead to narrowing of the channels or the tube itself.

In some embodiments, the spaced-apart elements are closed-loop elements (e.g. rings) surrounding the flexible tube.

In some embodiments, the spaced-apart elements include at least two openings positioned radially at equal distance one from another; such that at least a portion of one wire passes therethrough. The elements are stacked one above the other such that the openings are arranged in a concentric manner. A steering wire is threaded through all concentric holes of all the rings, one wire per each direction.

In some embodiments, at least one spaced-apart element has a cross-sectional geometrical shape defining a tapered section from both sides such that, while in a bent state when pulling on at least one steering wire, a U-shape of the tube is achieved. In this way, the creation of elbows, or folded portions, is prevented. The U-shape of the tube is determined by the distance between the spaced-apart elements and the angle of the tapered section.

In some embodiments, a portion of the steering wires is positioned within the flexible tube in the non-steerable portion of the tube and a portion of the steering wires passes through the spaced-apart elements. Each steering wire is configured to bend the tube respectively in one direction. At least one steering wire has one end fixed to one of an outermost spaced-apart element or the distal end of the tube, while the other end of the steering wire is free to move and is connected to a wire pulling device, which in some embodiments may be a mechanical joystick. The angle of the bend corresponds to the amount of the wire that was pulled out. Pulling the wire causes bending momentum in all the rings that it passes through.

In some embodiments, the device has three steering wires and the elements have three openings respectively positioned at 120° one from another. In other embodiments, the device has four steering wires and the rings have four openings respectively positioned at 90° one from another. In some embodiments, the end of the steering wire, being free to move, is connected to a joystick to thereby enable full control of the bending of the tube at any desired angle. The connection between the wires and the joystick may be made mechanically, electrically, hydraulically, or by using any possible connections known in the art.

In some embodiments, a part of the steering wires are enclosed by flexible spring-like sleeves (e.g. closed coil spirals) having at least one incompressible portion. In particular, the portion of the steering wires passing through the spaced-apart elements is not enclosed by the sleeves while the remaining portion passing through the tube may be enclosed by the sleeves.

In some embodiments, one end of the sleeve is fixed near the proximal end of the tube to the first spaced-apart element and the other end is connected to a wire pulling mechanism that serves as an anchor. Bends of the tube cause the incompressible part of spring-like sleeve to move in or out of the tube, thus the sleeve has to be longer than the tube in order to allow free movement of the sleeve. The sleeves are positioned radially and concentrically to the openings of the steering rings.

In some embodiments, the flexible tube encloses a plurality of channels passing therethrough, at least a portion of a spring-like sleeve being arranged for sliding movement through a channel respectively. The channels are configured as openings along the flexible tube. The channels may accommodate auxiliary tubes. In some embodiments, the flexible tube comprises a plurality of tubes passing therethrough configured for at least one of supplying water, supplying electricity, venting fluid outside the lumen and controlling various inflatable device ("balloon") pressures, sensing various inflatable device ("balloon") pressures, and sensing body lumen's pressures (e.g., sensing pressure distal to apparatus). In this connection, it should be understood that this multi-lumen configuration alters the flexibility of the flexible tube. As described above, the distance between the spaced-apart elements is determined such that the distal end of the tube could be deflected to any desired angle in the range of 0 to 180°, while not obstructing the flows in multi-lumen channels. Because the flexible tube comprises a plurality of auxiliary tubes passing therethrough configured for supplying fluids, the bending of the tube is appropriately selected such that the fluid flow supplied through the channels would not be impeded. Therefore, the distance between the space-apart elements is selected to prevent a sharp angular pipe fitting or a folded portion of the tube. For example, the auxiliary tubes may be electrical cables, hollow tubes shaped to define a lumen for passage therethrough of a tool, or hollow tubes shaped to define a lumen for passage therethrough of a fluid. The tool passing through the channel may be selected from at least one of an imaging device, an illumination device, a biopsy collecting tool, an optical device, a fluid device, and a treatment tool.

As described above, the steering device of the present invention may also be an integral part of an endoscopic system comprising an image capturing device which is steered to any desired destination to enable to image a body lumen. The steering device is configured and operable to bend the flexible distal end of the endoscopic system such that a space is created between the body lumen and an image-capturing device to facilitate imaging of the body lumen.

According to another broad aspect of the present invention, there is provided a steering device for use in a body lumen of a patient, comprising: a flexible tube; at least two steering wires having at least a portion passing within the flexible tube; at least two spring-like sleeves; each spring-like sleeve at least partially enclosing a steering wire respectively; wherein the spring-like sleeve has a variable pitch along its length; such that the flexible tube comprises at least two portions having different bending properties.

In some embodiments, the steering wires are enclosed by spring-like sleeves having a different step/pitch along its length defining two portions having different bending properties. In this configuration, one end of each steering wire is rigidly fixed to the distal end (e.g. tip) while the other end of the steering wire is free to move and connected to a wire pulling device, which in some embodiments may be a mechanical joystick. The steering wires are configured and operable to steer the bending portion of the tube by pulling at least one end of at least one steering wire outside the tube. The bending of the tube is provided by compressing one side (the bending side) and stretching the other (outer to the bend). Each steering wire bends the tube's portion in one direction. To obtain a full steering in any direction, at least three steering wires are generally required.

BRIEF DESCRIPTION OF THE FIGURES

In order to understand the invention and to see how it may be implemented in practice, preferred embodiments will now be described, by way of non-limiting example only, with reference to the accompanying drawing, in which FIG. 1 schematically illustrates the steering device of the present invention according to some embodiments of the present invention;

FIG. 6 schematically illustrates the steering device of the present invention incorporated in an endoscopic system having two inflatable balloons;

DETAILED DESCRIPTION OF EMBODIMENTS

Figure 1:
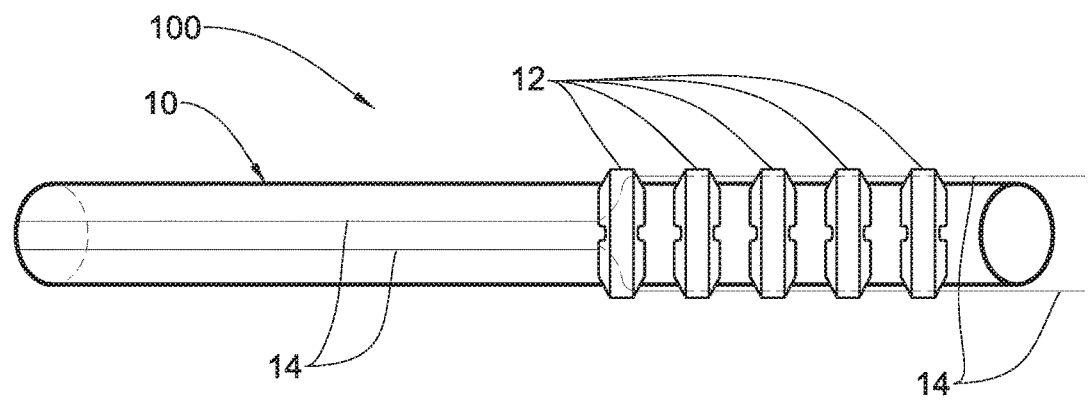

Reference is made to FIG. 1 illustrating one possible configuration of the steering device of the present invention according to one embodiment of the present invention. The steering device is integrated with a flexible tube and is configured to direct and orient the distal end of the tube in any desired direction and at any desired angle. In particular, the invention relates to a novel steering device being configured and operable to direct and orient the tip of a tool within a body lumen to facilitate steering of the tool from outside of the patient's body. The steering device 100 for use in a body lumen of a patient, comprises a flexible tube 10, a plurality of spaced-apart elements 12 positioned along at least a portion of the tube 10, and at least two steering wires 14 having at least a portion passing through the spaced-apart elements 12 and at least a portion passing within the flexible tube 10. The spaced-apart elements 12 and the tube 10 form a single integrated unit.

Each steering wire 14 bends the tube's portion in one direction. Each steering wire 14 is configured to transfer a pulling force to the distal end of the flexible tube 10 in order to bend it. To obtain a full steering in any direction, at least three steering wires are generally required. One end of each steering wire is rigidly fixed to the tube or to the outermost spaced-apart element while the other end of the steering wire is free to move. The steering wires 14 are configured and operable to steer the bending portion of the tube in which the spaced apart elements 12 are incorporated by pulling at least one end of at least one steering wire outside the tube. The steering device provides the steering capability of being displaced to any direction and being bent to any angle. The bending of the tube is provided by compressing one side (the bending side) and stretching the other (outer to the bend).

As illustrated in FIG. 1, at the non-steerable part of the tube, the steering wires 14 are positioned within the flexible tube. At the steerable part of the tube in which the spaced apart elements 12 are incorporated, the steering wires exit the tube and are threaded through the spaced-apart elements

12. At the steerable part of the tube, the other part of the steering wires 14 is thus positioned around the flexible tube 10.

The spaced-apart elements 12 are rigidly fastened along the tube 10. The fastening of the elements on the tube may be made by any suitable method for example by at least partially coating the element with adhesive material or by ultrasonic welding. Alternatively the elements and the tube may be manufactured to form a single integrated unit.

The spaced-apart elements 12 are rigidly fastened along the tube and may be separated by a variable distance between them. In some embodiments, the spaced-apart elements 12 are rigidly fastened along the tube and are separated by a constant distance between them. The distance between the elements determines the properties of the tube such as its flexibility and bending properties as well as the shape of the bent tip. The distance between the spaced-apart elements is determined according to the specific material of the flexible tube.

In some embodiments, the flexible tube 10 comprises a plurality of steering channels passing therethrough (illustrated in FIGS. 7A-7C) configured for accommodating at least a portion of the steering wire being arranged for sliding movement therethrough. The tube 10 may be made of a block copolymer such as Pebax™, thermoplastic polyurethane (TPU) or other materials.

The flexible tube 10 may comprise at least one of an electrical cable, a hollow tube shaped to define a lumen for passage therethrough of a tool, and a hollow tube shaped to define a lumen for passage therethrough of a fluid as will be described below with respect to FIGS. 7A-7C. This multi-lumen configuration alters the flexibility of the flexible tube. Moreover, it should be understood that the distance between the spaced-apart elements is determined such that the distal end of the tube could be deflected to any desired angle in the range of 0 to 180°, while not obstructing the flows in multi-lumen channels. By using the novel configuration of the steering device in which the steering rings are integrated with a flexible tube and not mounted on another tube enables to provide a steering device with higher flexibility and in which minimal deflection force has to be applied in order to bend the bending portion of the tube.

Figure 2A:
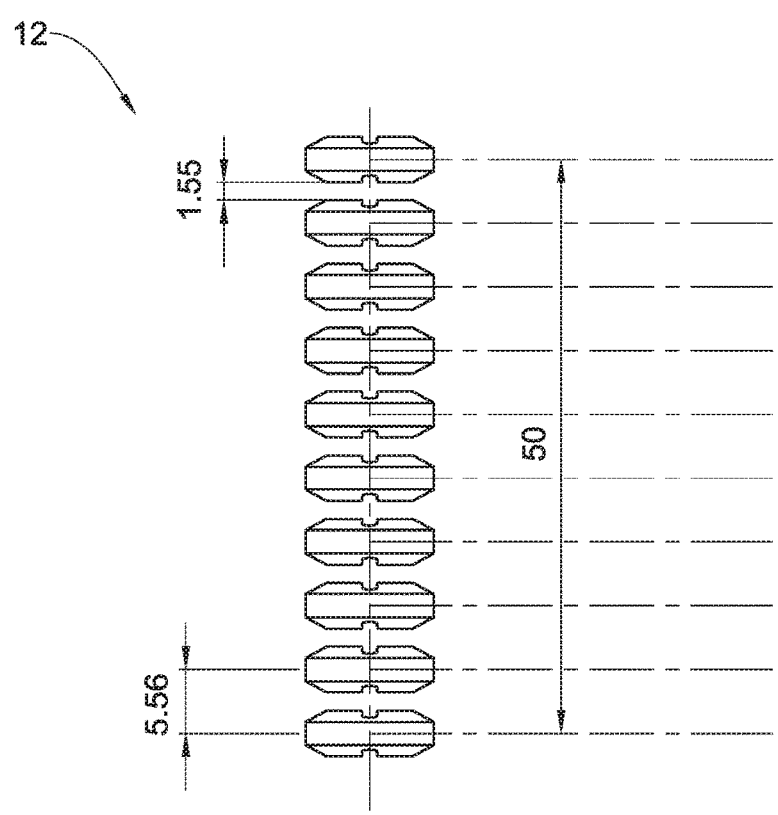
FIGS. 2A-2E illustrate more specifically the spaced-apart elements of the steering device of the present invention.
Figure 2B:
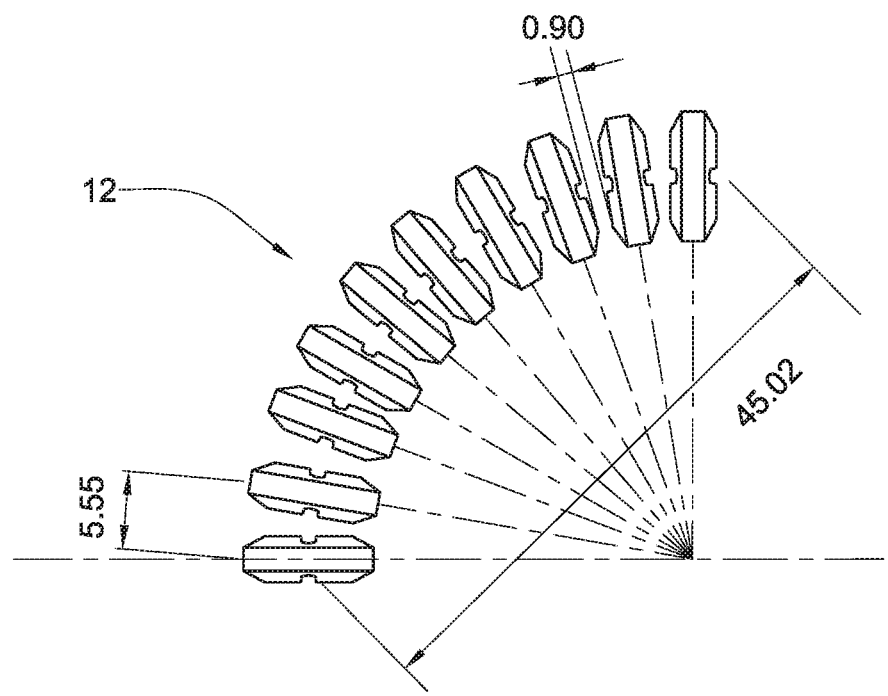
Figure 2C:
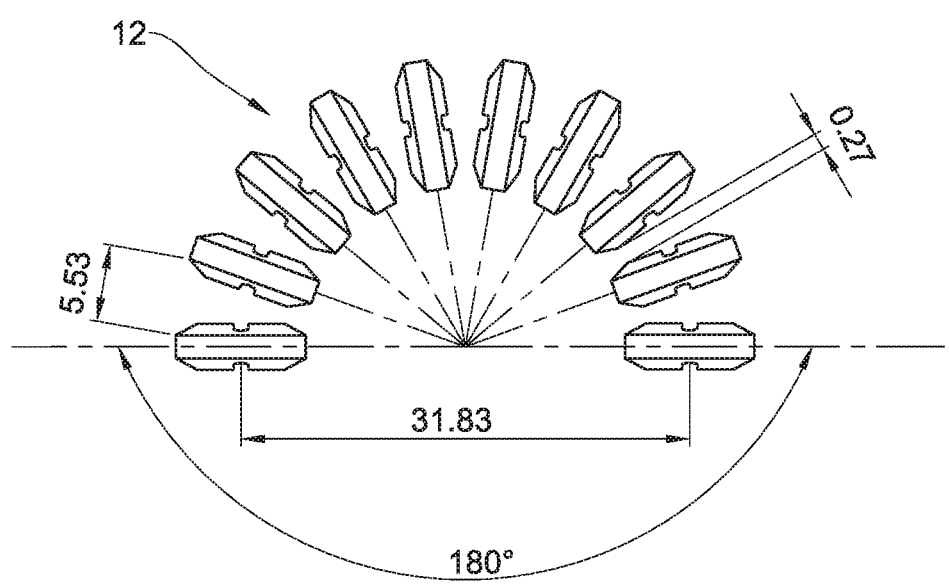

Reference is made to FIGS. 2A-2D illustrating one possible configuration of the elements 12 having a closed-loop configuration surrounding the flexible tube and configured to be threaded by the steering wires. Although the elements are represented as having a ring-like shape configuration, any shape matching the external shape of the flexible tube may also be used. For clarity of illustration, in these figures, the tube on which the rings are fastened, as well as the steering wires, is not shown. FIG. 2A illustrates the straight state (non-bent) in which the rings do not touch each other. FIG. 2C illustrates a fully bent state in which the ring's edges come into contact. FIG. 2B illustrates an intermediate state in which the rings are steered in one direction. One end of a wire is fixed to the outermost ring while the other end of the steering wire is free to move. Pulling the wire causes bending momentum in all the rings that it passes through, as illustrated in FIG. 2B.

As described above, the appropriate selection of the distance between the elements enables an optimal steering in any direction and at any angle. In a non-limiting example, as illustrated in FIG. 2A, the distance between the external surfaces of the rings has been selected to be in the range of about 1.5-1.55 mm. The distance between the centers of the rings has been selected to be in the range of about 5-6 mm. The length of the steerable portion of the tube in which the rings are incorporated has been selected to be in the range of about 50-60 mm. The length of the tube may be about 2.5 m. The amount of the spaced-apart elements may be variable and depends on the required maximal bending radius, multi-lumen tube flexibility and the width of each spaced-apart element.

Figure 2D:
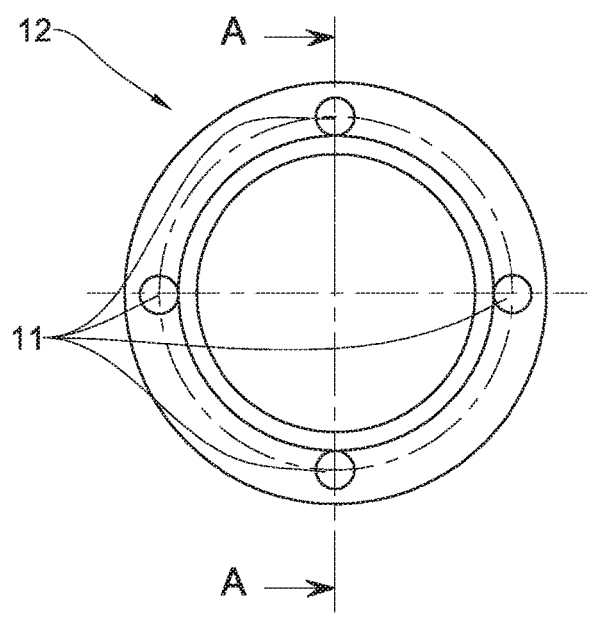
Figure 2E:
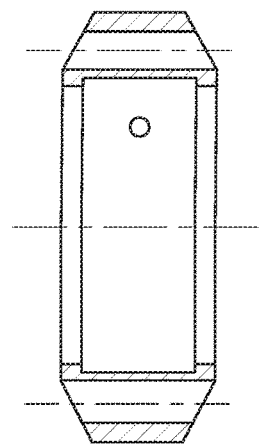

Reference is made to FIGS. 2D-2E illustrating cross-sections of the ring-like element 12. As illustrated in FIG. 2D the ring-like element has four openings positioned radially at equal distance one from another (at 90°) through which at least a portion of the steering wires is intended to pass. Generally, each ring contains at least two openings positioned radially at equal distance one from another. The rings are stacked one above the other such that the openings are arranged in a concentric manner. A steering wire is threaded through all concentric holes of all the rings, one wire per each direction. FIG. 2E illustrates the ring-like element according to the cross section marked A-A in FIG. 2D. As illustrated in FIG. 2E, in some embodiments, the ring-like element is configured such that its cross-sectional shape defines a tapered section from both sides to ensure that while in a bent state when pulling on the steering wires, a U-shape of the tube would be achieved to prevent the creation of elbows or folded portions.

Figure 3:
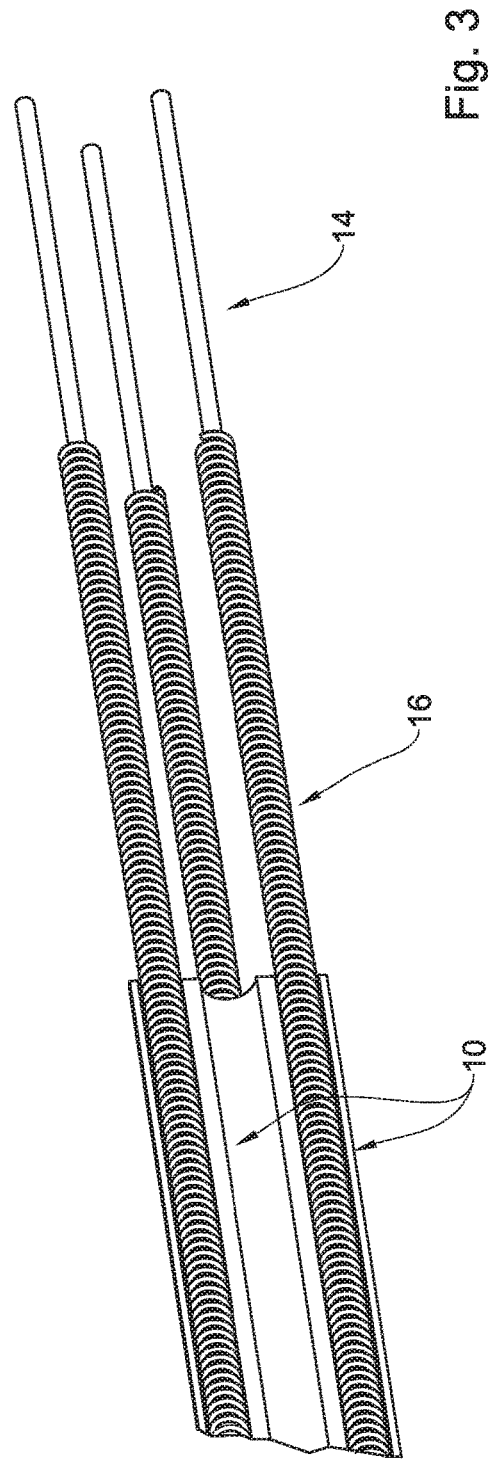
FIG. 3 shows the configuration of the steering wire enclosed by a spring sleeve according to a specific example of the invention.

Reference is made to FIG. 3 illustrating an example of the steering wires having at least a portion positioned along the length of the flexible tube 10. FIG. 3 illustrates three steering wires 14 at least partially enclosed by the spring-like sleeves 16 respectively. The portion of the steering wires 14 passing through the spaced-apart elements (not shown in this figure) is not enclosed by the sleeves 16 while the remaining portion passing through the tube is enclosed by the sleeves 16. The spring-like sleeves 16 may be flexible closed coil spirals having an incompressible part that allow sliding movement of steering wires inside. The steering wires at least partially enclosed by the spring-like sleeves may be configured as a Bowden cable. It should be noted that, as well known in the art, a Bowden cable is a type of flexible cable used to transmit mechanical force or energy by the movement of an inner cable (most commonly of steel or stainless steel) relative to an hollow outer cable housing. In the present invention, the inner cable is the steering wire and the housing is the spring-like sleeves. The housing is generally of composite construction, consisting of a helical steel wire, often lined with nylon, and with a plastic outer sheath. The linear movement of the inner cable is most often used to transmit a pulling force. Therefore, the spring-like sleeve may be made of a close-wound helix of round or square steel wire. This makes a flexible housing but causes the length to change as the housing flexes. Because on the inside of the bend the turns of a close-wound helix cannot get any closer together, the bending causes the turns to separate on the outside of the bend, and so at the centerline of the housing, there must also be an increase of length with increasing bend. Moreover, in the present invention the steering wire and the spring-like sleeve are located far from the center of the flexible tube that may bend in loops to fit to the colon. Bending a lumen compresses on inner side of the bend and stretches the outer side to the bend. Since the spring-like sleeve is unable to be compressed, only one end of the spring-like sleeve is rigidly fixed to the tube and the other end is free to move to compensate for the inability to compress.

Figure 8:
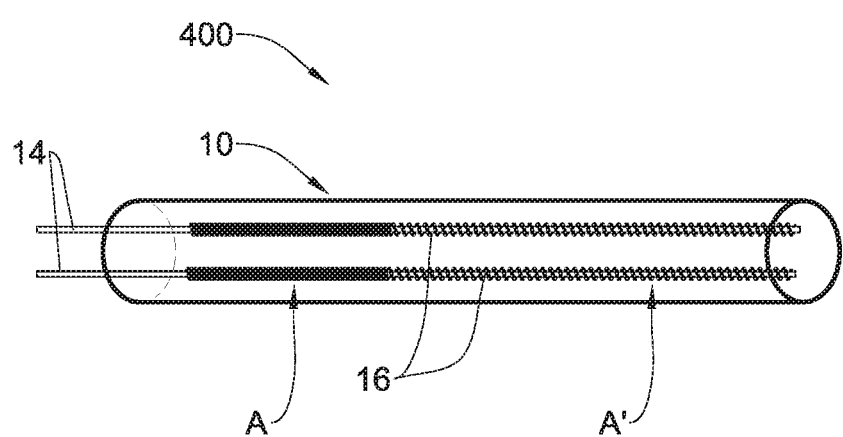
FIG. 8 schematically illustrates the steering device of the present invention according to some embodiments of the present invention.

As will be also described with respect to the embodiment of illustrated in FIG. 8, the sleeve may be a closed-coil (e.g. having zero distance between the coils) being rigid in the direction of the pulling force of the steering wire but still remaining flexible if one wants to bend the sleeve in all directions. In a specific and non-limiting example, the sleeve can be made of metal.

The sleeve may partially or completely enclose the steering wire. In a specific and non-limiting example, the wire is not enclosed in about the last 50 mm of the flexible tube. This portion is threaded through the spaced-apart elements.

When the wire is pulled, it slides backward and pulls the distal end of the flexible tube aside in order to bend the distal tip. The bending length of the tip is defined by the length of the exposed (non-enclosed) wire. The sleeve prevents propagation of the bend to areas that must not be bent. The length of the exposed portion of the wire is defined according to the desired bending radius of the flexible tube.

Figure 4:
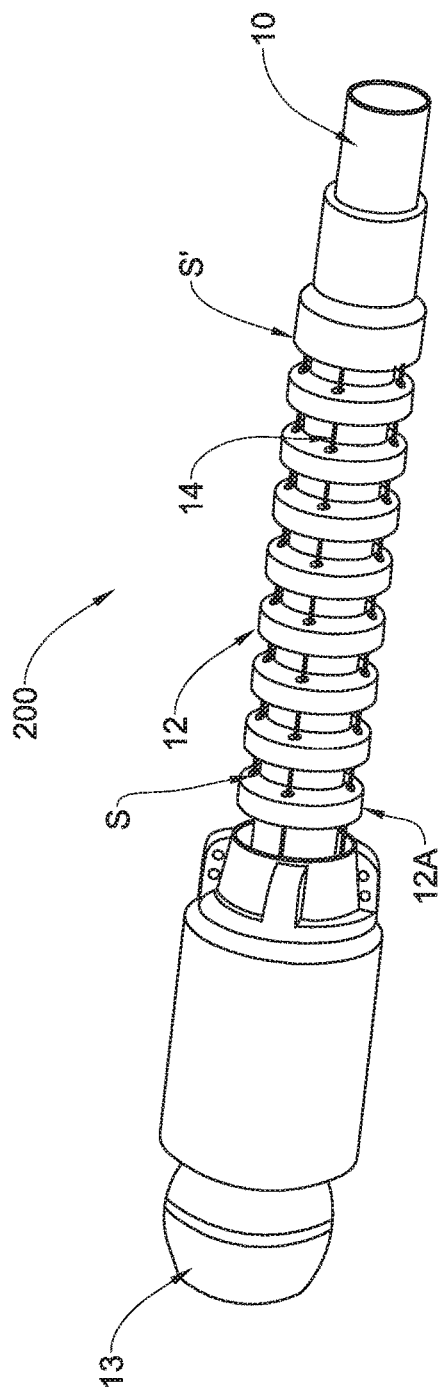
FIG. 4 is a graphical representation of the steering device of the present invention incorporated in an endoscopic system.

The sleeves are positioned radially and concentrically to the openings of the steering rings. To reduce the friction forces between the spring-like sleeve and the steering wires, any lubricant known in the art, such as Teflon™ (PTFE) powder, may be used. Reference is made to FIG. 4 illustrating an example of the steering device of the present invention incorporated in an endoscopic system.

The steering device 200 may be an integral part of an endoscopic system, or an endoscopic tool which may pass through the flexible tube 10. In this specific and non-limiting example, the endoscopic tool comprises an image capturing device 13. Although only an image-capturing device is illustrated, the steering device may comprise a tool selected from at least one of an imaging device, an illumination device, a biopsy collecting tool, an optical device, a fluid device, and a treatment tool. The image capturing device 13 may then be steered to any desired destination to enable to image a body lumen (not shown). The steering device 200 is configured and operable to steer the image capturing device 13 such that a space is created between the body lumen and the image-capturing device 13 to facilitate the imaging of the body lumen. As described above, the steering device 200 comprises a flexible tube 10, a plurality of spaced-apart steering rings 12 positioned along at least a portion of the tube 10 and at least two steering wires 14 having at least a portion passing through the spaced-apart steering rings 12 and at least a portion passing within the flexible tube 10. One end of the steering wire 14 is fixed near the distal end of the tube (shown as S) to the last/outermost steering ring 12A and the other end of the steering wire 14 is free to move. One end of the spring-like sleeve is fixed near the proximal end of the tube to the first steering ring S' and the other end of the spring-like sleeve is anchored at a wire pulling device (marked as S" in FIG. 5). The first steering ring S' has a different shape that the other rings to be able to be connected to the tube 10.

Figure 5:
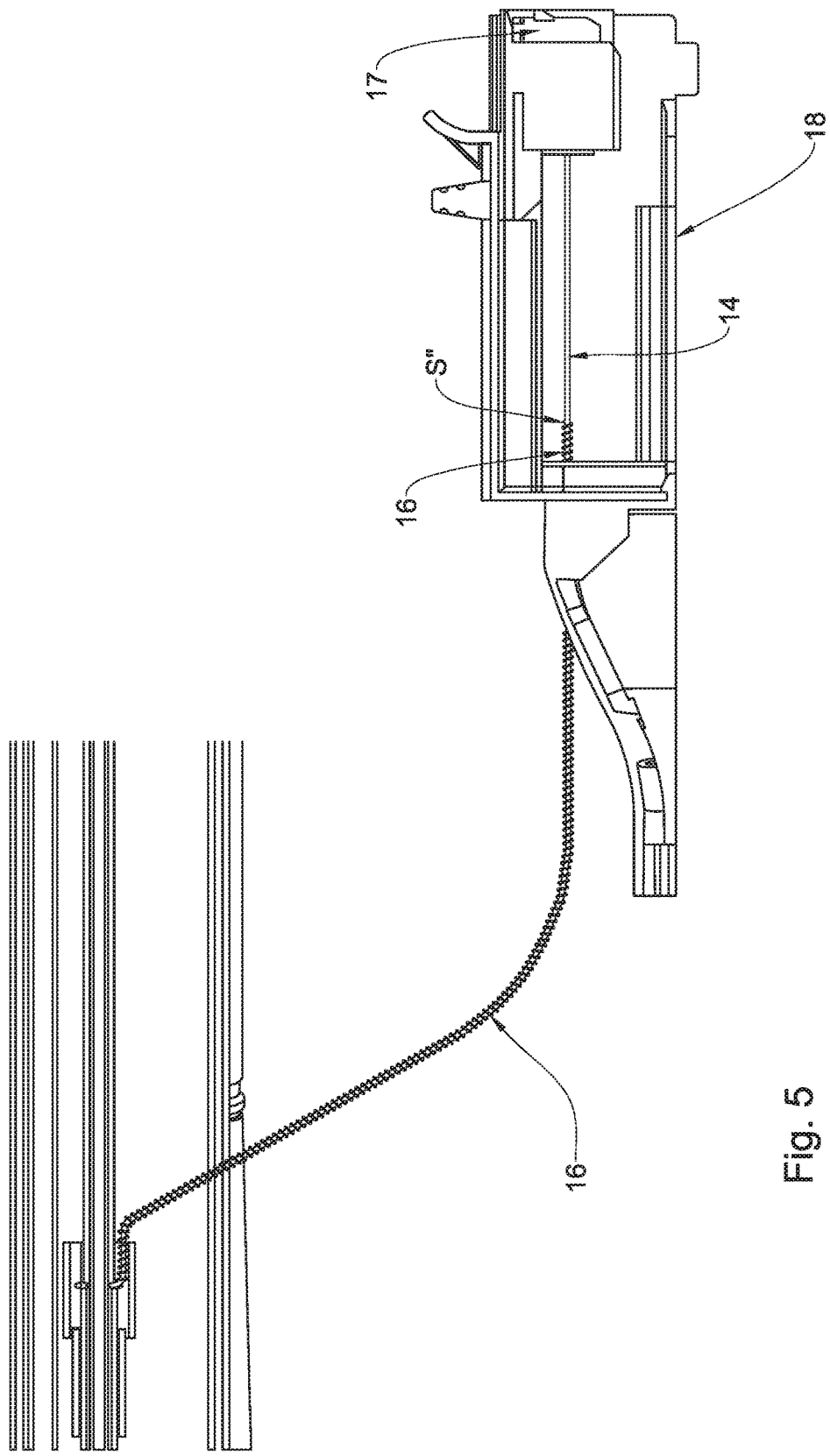
FIG. 5 illustrates the connection between a steering sleeve and a wire pulling device according to a specific example of the invention.

For example, the steering portion of the device has been selected to be in the range of about 50-60 mm. The distance between the external surfaces of the rings has been selected to be in the range of about 1.5-1.55 mm. In some embodiments, the steering device can be manipulated by a wire pulling enabling full control of the steering of the tube. As illustrated in FIG. 5, one end of the steering wires 14 is connected to the outside of the tube via a connection mechanism 18 to a wire pulling device such as a mechanical joystick (not shown) which enables full control of the bending of the tube at any desired angle. The steering wires 14 are at least partially enclosed by the spring-like sleeves 16 respectively. The extremity of the steering wire 14 is connected to a pulley 17 that is pulled to bend the tube. The pulling of the wires 14 may be made mechanically, electrically, hydraulically or by using any possible connections known in the art. It should be noted that although only one steering wire and one respective sleeve are represented, the steering device comprises at least two steering wires connected to the wire pulling device in the same way.

Reference is made to FIG. 6 representing the steering device of the present invention integrated with a GI tool as described in previous GI View patent and patent applications. As shown, the tool comprises inter alia a piston head 304 coupled to a distal portion of the steering device 300 and adapted to form a pressure seal with a wall of the lumen after the carrier has been inserted into the lumen, and be advanced distally through the body lumen in response to pressure from the fluid pressure source. FIG. 6 shows two balloons 302 and 304 mounted on the tube 10 and having different diameters. The smaller balloon 304 has a sleeve-like protrusion shape configured to enclose the spaced-apart elements 12 and being rigidly fixed to the flexible tube 10. In order to prevent gas leakage out of the balloon 304 through the steering wires, another sheet sleeve 13' surrounds the steering device 300 and seals the steering device 300 from the balloon 304. It should be noted that as illustrated in the figure a part or whole of the sleeve 13' may be surrounded by the piston head 304. Since, in this configuration, the sleeve exits the tube underneath the piston head 304, the part of the sleeve 13' surrounded by the piston head 304 enables to inflate the piston head and to prevent the inflation gas escape through the sleeve to the lumen.

The tool may also comprise an auxiliary piston head balloon 302 positioned outside the steering device 300 proximal to the first-mentioned piston head 304. The auxiliary piston head 302, which may be inflatable, may be fixed axially to the carrier at a fixed distance from the first-mentioned piston head 304. The auxiliary piston head 302 is adapted to be inflated so as to attain and maintain direct contact with the wall of the body lumen, and at at least one time while the carrier is within the body lumen, the distal piston head 304 is adapted to be in a state of being already deflated at least in part simultaneously with the auxiliary piston head 302 being already inflated and being advanced distally through the colon in response to pressure from the fluid pressure source, and at at least one other time while the carrier is within the body lumen, the auxiliary piston head 302 is adapted to be in a state of being already deflated at least in part simultaneously with the distal piston head 304 being already inflated and being advanced distally through the colon in response to pressure from the fluid pressure source.

Figure 7A:
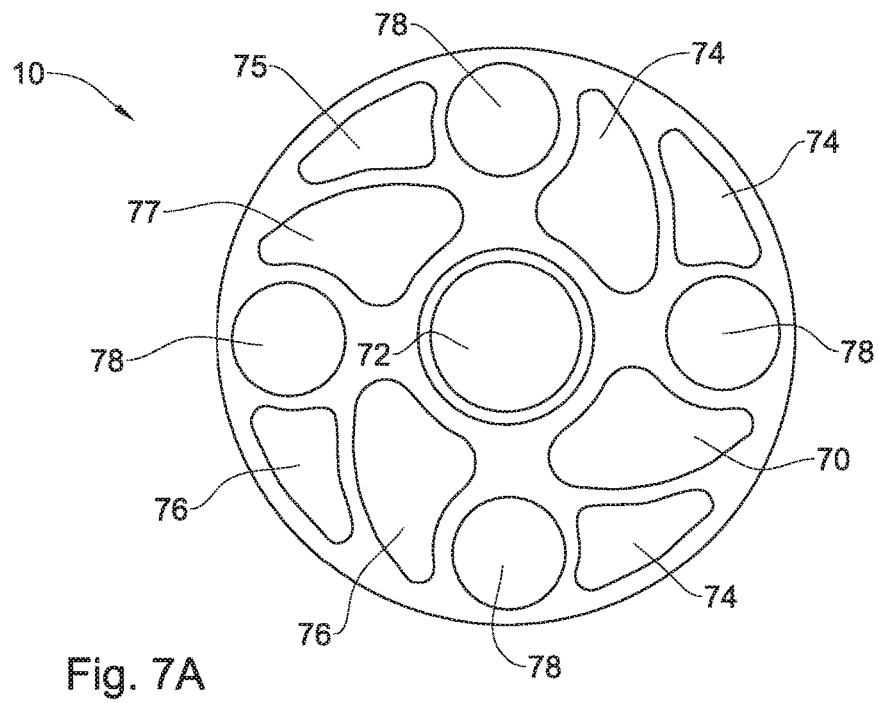
FIGS. 7A-7C schematically illustrates different views of the tube of the steering device of the present invention according to some embodiments of the present invention.
Figure 7B:
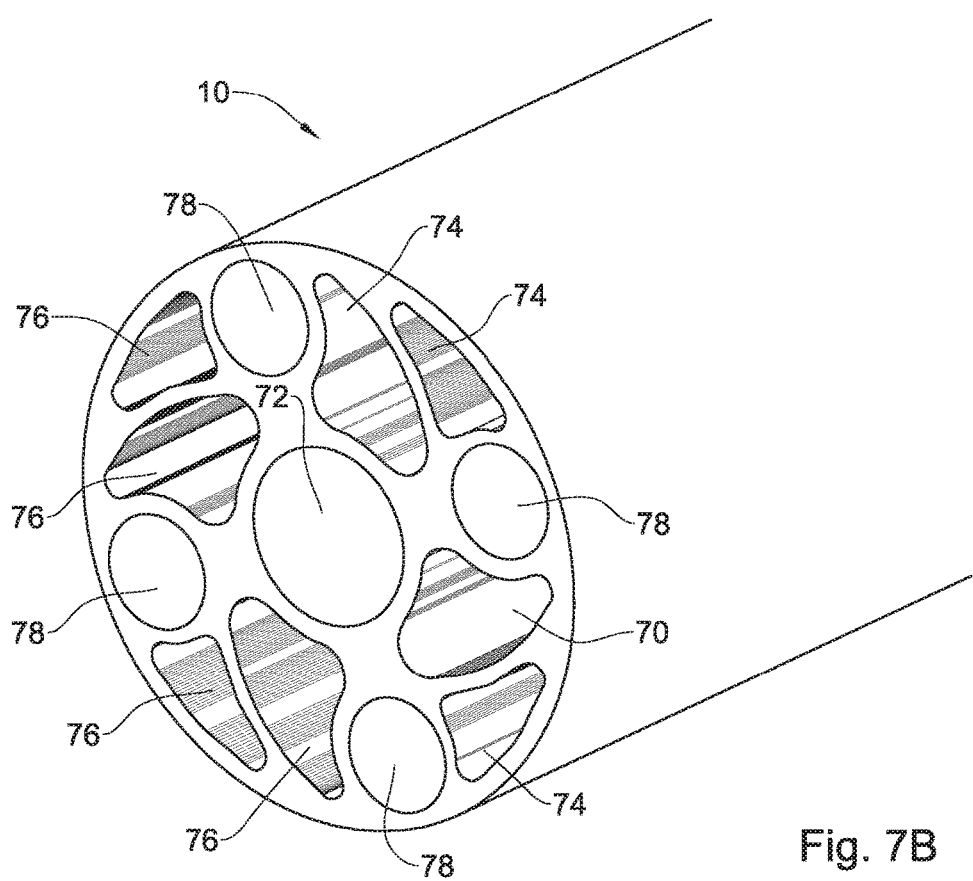
Figure 7C:
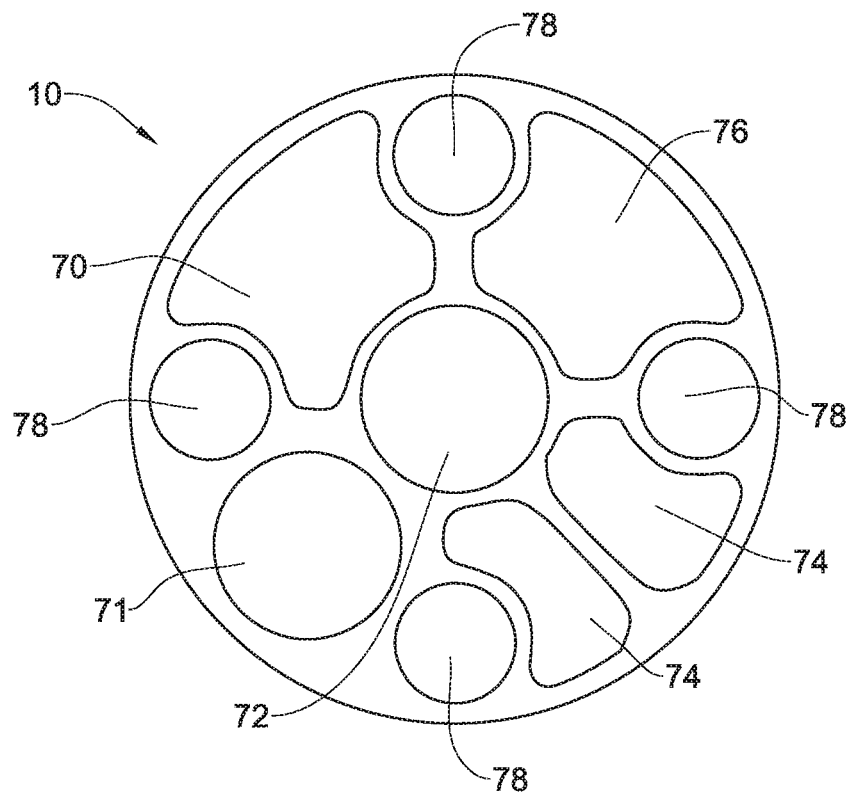

Reference is made to FIGS. 7A-7C schematically illustrates different views of the tube of the steering device of the present invention according to some embodiments of the present invention. In some embodiments, the flexible tube 10 comprises a plurality of channels through which a plurality of auxiliary tubes may pass. In some embodiments, the flexible tube 10 comprises at least two steering channels 78 for accommodating therein at least two steering wires respectively. In some embodiments, the steering channels 78 also accommodate the spring-like sleeves. The channels may be configured for supplying water 70 and inflating at least one inflatable device 74 (e.g. piston head 304 and auxiliary piston head balloon 302 of FIG. 6). The flexible tube 10 may also comprise at least one suction channel 76 that may comprise a vent tube through which fluid is ventable to the outside. The vent tube may pass through an inflatable balloon and have an opening distal to the balloon. Additionally or alternatively, the suction channel 76 may be adapted to be coupled to a suction source, whereby to actively facilitate the passage of the fluid out of the lumen. The flexible tube 10 may also comprise an electrical channel 72 configured for at least one of transmitting an image (e.g. video) from the image capturing device on the tip of the device, illuminating the body lumen (e.g. colon), controlling various inflatable device ("balloon") pressures sensing various inflatable device ("balloon") pressures, and sensing body lumen's pressures (e.g., sensing pressure distal to apparatus). FIG. 7B illustrates a perspective view of the cross section of the flexible tube 10 according to a specific and non-limiting example of FIG. 7A. FIG. 7C illustrates another example in which the flexible tube 10 includes a water channel 70, an electrical channel 72, four steering channels 78 for accommodating the steering wires and optionally the sleeve respectively, a suction (venting) channel 76 configured facilitate the passage of fluid and particles out of the lumen, at least one inflation channel 74 for inflating at least one inflatable device respectively and a tool channel 71 being configured as a hollow tube shaped to define a lumen for passage therethrough of a tool. This multi-lumen configuration alters the flexibility of the flexible tube. It should be understood that because the flexible tube comprises a plurality of tubes passing therethrough configured for supplying fluids, the bending of the tube is appropriately selected such that the fluid flow supplied through the tubes will not be impeded. Therefore, the distance between the space-apart elements is selected to prevent a sharp angular pipe fitting or a folded portion of the tube.

Figure 9:
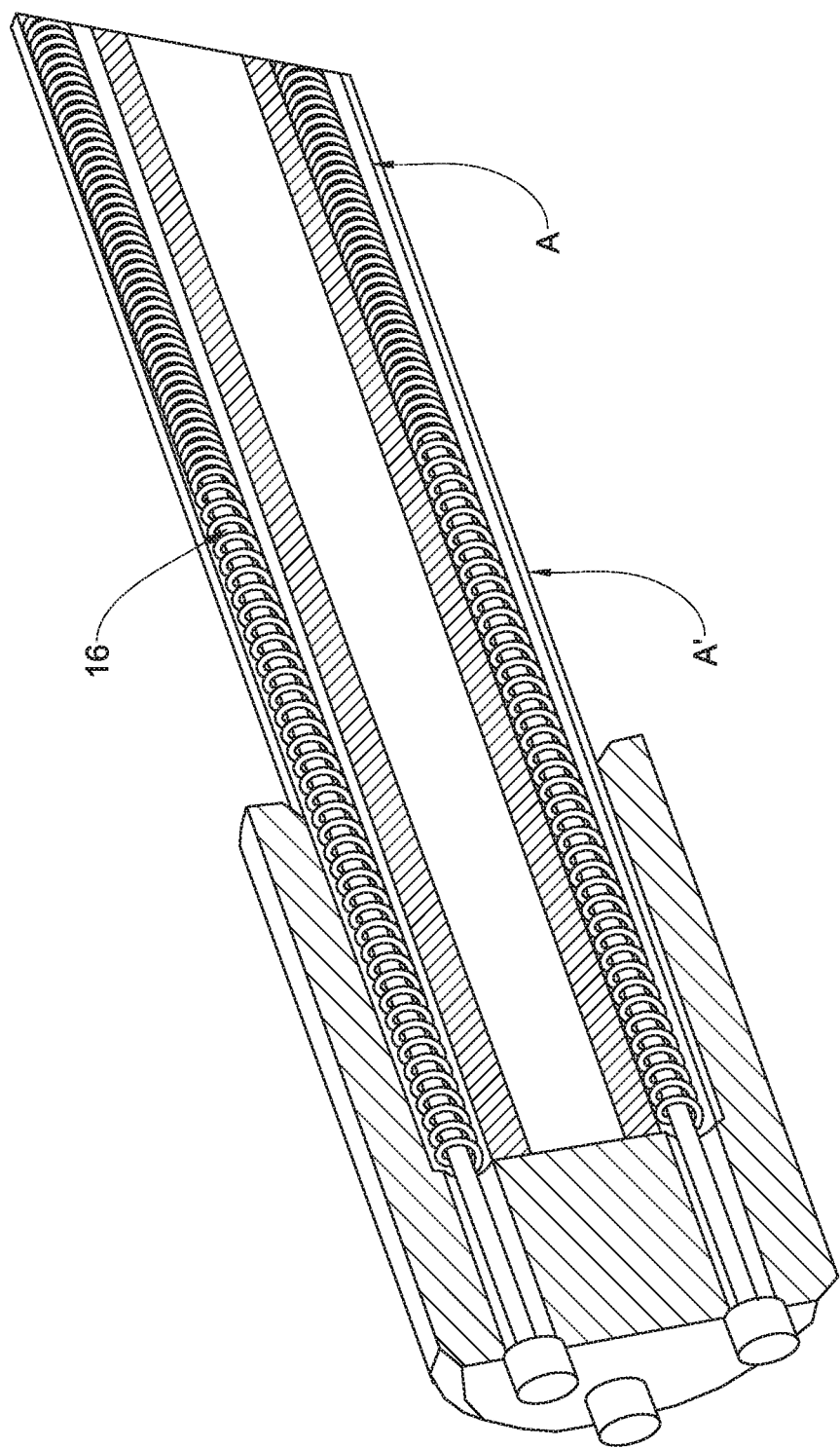
FIG. 9 shows the configuration of the steering wire enclosed by a spring sleeve according to a specific example of the invention.

Reference is made to FIG. 8 illustrating the steering device of the present invention. The steering device 400 is configured to direct and orient the distal end of the tube in any desired direction and at any desired angle. In particular, the invention relates to a novel steering device being configured and operable to direct and orient the tip of a tool within a body lumen to facilitate steering of the tool from outside of the patient's body. The steering device 400 comprises a flexible tube 10 having two portions (marked as A and A') of different bending properties and at least two steering wires 14 passing within the tube 10; and at least two spring-like sleeves 16, each spring-like sleeve 16 at least partially enclosing a steering wire respectively. The spring-like sleeve 16 has a variable pitch along its length. In this connection, it should be understood that, according to some embodiments of the present invention, the steering device 400 does not include the spaced-apart elements, reducing the total diameter of the system. However, using this configuration renders the portion of the flexible tube containing the exposed wire (the one that bends) too flexible and may create sharp kinks that might disrupt fluid flow in the plurality of auxiliary channels of the multi-lumen tube. Therefore, to stiffen the flexible part of the tube, the spring-like sleeves are extended to cover the exposed part of the wire. This extension may be made by another spring fixed to the first one or may be made by using one integral spring having a variable pitch. The part of the sleeve enclosing the bending portion of the tube has compressible coils with non zero distance between coils that can be compressed to thereby enable bending of the distal end of the tube. The remaining part of the sleeve has fully compressed coils. In this specific and non-limiting example, a part of the spring-like sleeve 16 that is positioned in the A portion has a zero distance between the coils, thus cannot be compressed and stays rigid permanently. The part of the spring-like sleeve 16 in the A' portion has a non-zero distance between the coils, thus is able to be compressed. Pulling the steering wire causes the distal end (e.g. tip) of the tube 10 to bend at the A' portion but not at the A portion because of the different bending properties. In the A' portion, the distance between the coils can be variable (or constant) in order to define the required bending radius. In some embodiments, portions A and A' may comprise two different spring-like sleeves stacked on top of the other. Reference is made to FIG. 9 illustrating another embodiment of the present invention in which the steering wires are enclosed by spring-like sleeves 16 having a different step/pitch along their length defining two portions A and A' having different bending properties. This configuration provides a non-uniform flexibility along the tube's length that allows the distal end of the tube to be bent while the more proximal regions of the tube have relatively low bending properties. As illustrated, one end of each steering wire is rigidly fixed to the tube while the other end of the steering wire is free to move. The steering wires are configured and operable to steer the bending portion A' of the tube (having relatively high bending properties) by 0 to 180 degrees and more by pulling at least one end of at least one steering wire outside the tube. The A' portion is defined as the bending portion of the tube and has relatively high bending properties while the A portion is a bending portion having relatively low bending properties and cannot be bent. The A portion comprises a closed coil spring and the A portion comprises an open coil spring. The bending of the tube is provided by compressing one side (the bending side) and stretching the other (outer to the bend).

The invention claimed is:

1. A steering device for use in a body lumen of a patient, the steering device comprising:
   a single integrated unit formed by a flexible tube having a distal end portion and a plurality of spaced-apart elements configured to enable steering of the single integrated unit, said plurality of spaced-apart elements being located in a spaced-apart arrangement along an outer surface of at least the distal end portion of the flexible tube, said plurality of spaced-apart elements being rigidly fastened along the flexible tube and projecting outwardly from said outer surface of said flexible tube, said flexible tube passing through each of said plurality of spaced-apart elements; distances between the spaced-apart elements being selected in accordance with material of the flexible tube, said distances between the spaced-apart elements determining flexibility and bending properties of said distal end portion of the flexible tube; and
   at least two steering wires having at least a portion passing around the flexible tube and through said plurality of elements and at least a portion passing within said flexible tube; each of the at least two steering wires being configured to cause the bending of said at least distal end portion of the flexible tube together with the spaced-apart elements thereof until edges of the spaced-apart elements come into contact.

2. The steering device of claim 1, wherein said plurality of spaced-apart elements have at least one of the following configurations: a) said plurality of spaced-apart elements are separated by a constant distance; b) said plurality of spaced-apart elements are closed-loop elements surrounding the flexible tube; or c) said plurality of spaced-apart elements include at least two openings positioned radially at substantially equal distance one from another; such that at least a portion of one wire passes therethrough.

3. The steering device of claim 2, wherein said constant distance is selected to prevent at least one of a sharp angular pipe fitting or a folded portion of the flexible tube.

4. The steering device of claim 1, wherein at least one of the plurality of spaced-apart elements has a cross-sectional geometrical shape defining a tapered section from both sides such that while in a bent state when pulling on at least one steering wire, a U-shape of the flexible tube is achieved.

5. The steering device of claim 1, wherein said at least two steering wires have at least one of the following configurations: (i) at least one of the steering wires has one end fixed to one of an outermost element from said plurality of spaced-apart elements or to the flexible tube's distal end, while the other end of the steering wire is free to move; or (ii) each of the steering wires is configured to bend the tube respectively in one direction.

6. The steering device of claim 5, wherein said end of the steering wire is free to move and connected to a wire pulling device to thereby enable full control of the bending of the flexible tube at any desired angle.

7. The steering device of claim 1, wherein the at least two steering wires includes four steering wires.

8. The steering device of claim 1, further comprising at least one spring-like sleeve at least partially enclosing at least one of said steering wire, respectively.

9. The steering device of claim 8, wherein said flexible tube encloses a plurality of channels passing therethrough; at least a portion of the at least one spring-like sleeve being arranged for sliding movement through a channel respectively.

10. The steering device of claim 9, wherein said flexible tube includes at least one of an electrical cable, a hollow tube shaped to define a lumen for passage therethrough of a tool; and a hollow tube shaped to define a lumen for passage therethrough of a fluid.

11. The steering device of claim 8, wherein each of said at least one spring-like sleeve has a variable pitch along its length.

12. The steering device of claim 11, wherein said spring-like sleeve comprises a first portion having a closed coil spring and a second portion having an open coil spring.

13. The steering device of claim 11, wherein at least a portion of the spring-like sleeve is arranged for sliding movement through a respective channel inside the flexible tube.

14. The steering device of claim 1, further comprising at least one tool selected from at least one of an imaging device, an illumination device, a biopsy collecting tool, an optical device, a fluid device, or a treatment tool.

15. The steering device of claim 1, being an integral part of an endoscopic system including an image capturing device that is steerable to any desired destination to enable to image a body lumen.

16. The steering device of claim 1, wherein each of the plurality of spaced-apart elements is structurally independent from each other.

17. The steering device of claim 1, wherein each of the plurality of spaced-apart elements includes a closed-loop element surrounding the flexible tube.

18. The steering device of claim 17, wherein the closed-loop element includes a ring.

19. The steering device of claim 1, wherein the at least two steering wires pass through each and every one of the plurality of spaced-apart elements.

20. The steering device of claim 1, wherein the at least two steering wires pass through two or more of the plurality of spaced-apart elements.

21. The steering device of claim 1, wherein each of the plurality of spaced-apart elements extends about and is mounted to the flexible tube.

* * * * *